United States Patent [19]
Cox

[11] Patent Number: 6,083,232
[45] Date of Patent: *Jul. 4, 2000

[54] VIBRATING STENT FOR OPENING CALCIFIED LESIONS

[75] Inventor: Daniel L. Cox, Palo Alto, Calif.

[73] Assignee: Advanced Cardivascular Systems, Inc., Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/720,098

[22] Filed: Sep. 27, 1996

[51] Int. Cl.$^7$ ................................................... A61B 17/22
[52] U.S. Cl. ............................................. 606/128; 601/2
[58] Field of Search ...................... 601/2, 3, 4; 606/128

[56] References Cited

U.S. PATENT DOCUMENTS

| | | |
|---|---|---|
| 4,368,410 | 1/1983 | Hance et al. ................................. 601/2 |
| 4,438,622 | 3/1984 | Pons . |
| 4,439,185 | 3/1984 | Lundquist . |
| 4,439,186 | 3/1984 | Kuhl . |
| 4,446,867 | 5/1984 | Leveen et al. . |
| 4,468,224 | 8/1984 | Enzmann et al. . |
| 4,516,972 | 5/1985 | Samson . |
| 4,554,929 | 11/1985 | Samson et al. . |
| 4,577,631 | 3/1986 | Kreamer ....................... 601/2 |
| 4,582,185 | 4/1986 | Grimes et al. . |
| 4,616,652 | 10/1986 | Simpson . |
| 4,638,805 | 1/1987 | Powell . |
| 4,692,139 | 9/1987 | Stiles . |
| 4,748,982 | 6/1988 | Horzewski et al. . |
| 4,748,986 | 6/1988 | Morrison et al. . |
| 4,808,153 | 2/1989 | Parisi . |
| 4,827,943 | 5/1989 | Bornn et al. . |
| 4,870,953 | 10/1989 | DonMicheal et al. . |
| 4,898,575 | 2/1990 | Fischell et al. . |
| 4,898,577 | 2/1990 | Badger et al. . |
| 4,920,954 | 5/1990 | Alliger et al. . |
| 5,050,587 | 9/1991 | Sagara et al. ................................. 601/2 |
| 5,069,664 | 12/1991 | Guess et al. . |
| 5,209,799 | 5/1993 | Vigil . |
| 5,267,954 | 12/1993 | Nita . |
| 5,279,562 | 1/1994 | Sirhan et al. . |
| 5,312,328 | 5/1994 | Nita et al. . |
| 5,334,154 | 8/1994 | Samson et al. . |
| 5,336,234 | 8/1994 | Vigil et al. . |
| 5,368,557 | 11/1994 | Nita et al. . |
| 5,382,228 | 1/1995 | Nita et al. . |
| 5,405,318 | 4/1995 | Nita . |
| 5,417,672 | 5/1995 | Nita et al. . |
| 5,427,118 | 6/1995 | Nita et al. . |
| 5,458,613 | 10/1995 | Gharibadeh et al. . |
| 5,474,530 | 12/1995 | Passafaro et al. ........................... 601/2 |
| 5,484,449 | 1/1996 | Amundson et al. ......................... 601/2 |
| 5,527,336 | 6/1996 | Rosenbluth . |
| 5,542,917 | 8/1996 | Nita et al. . |
| 5,549,119 | 8/1996 | Solar . |
| 5,609,606 | 3/1997 | O'Boyle . |
| 5,611,807 | 3/1997 | O'Boyle . |
| B1 4,323,071 | 5/1990 | Simpson et al. . |

FOREIGN PATENT DOCUMENTS

| | | |
|---|---|---|
| 0 744 163 | 11/1996 | European Pat. Off. . |
| 4-45187 | 7/1992 | Japan . |
| 7/47135 | 2/1995 | Japan . |
| 7-67967 | 3/1995 | Japan . |
| WO 93/06780 | 4/1993 | WIPO . |
| WO 96/39955 | 12/1996 | WIPO . |

*Primary Examiner*—Jeffrey A. Smith
*Assistant Examiner*—Eduardo C. Robert
*Attorney, Agent, or Firm*—Fulwider Patton Lee & Utecht, LLP

[57] ABSTRACT

An intraluminal catheter and stent delivery system using vibratory energy to open calcified lesions. The catheter having an expandable stent mounted on a balloon portion thereof, is adapted to convey vibratory energy through the stent to a calcified lesion to facilitate crossing and dilating the lesion during a PTCA procedure. A vibratory energy source is transmitted through a flexible wire to provide vibratory energy to the stent, which in turn provides vibratory energy to a calcified lesion to thereby at least partially pulverize the lesion and assist in crossing and dilating the body lumen.

22 Claims, 5 Drawing Sheets

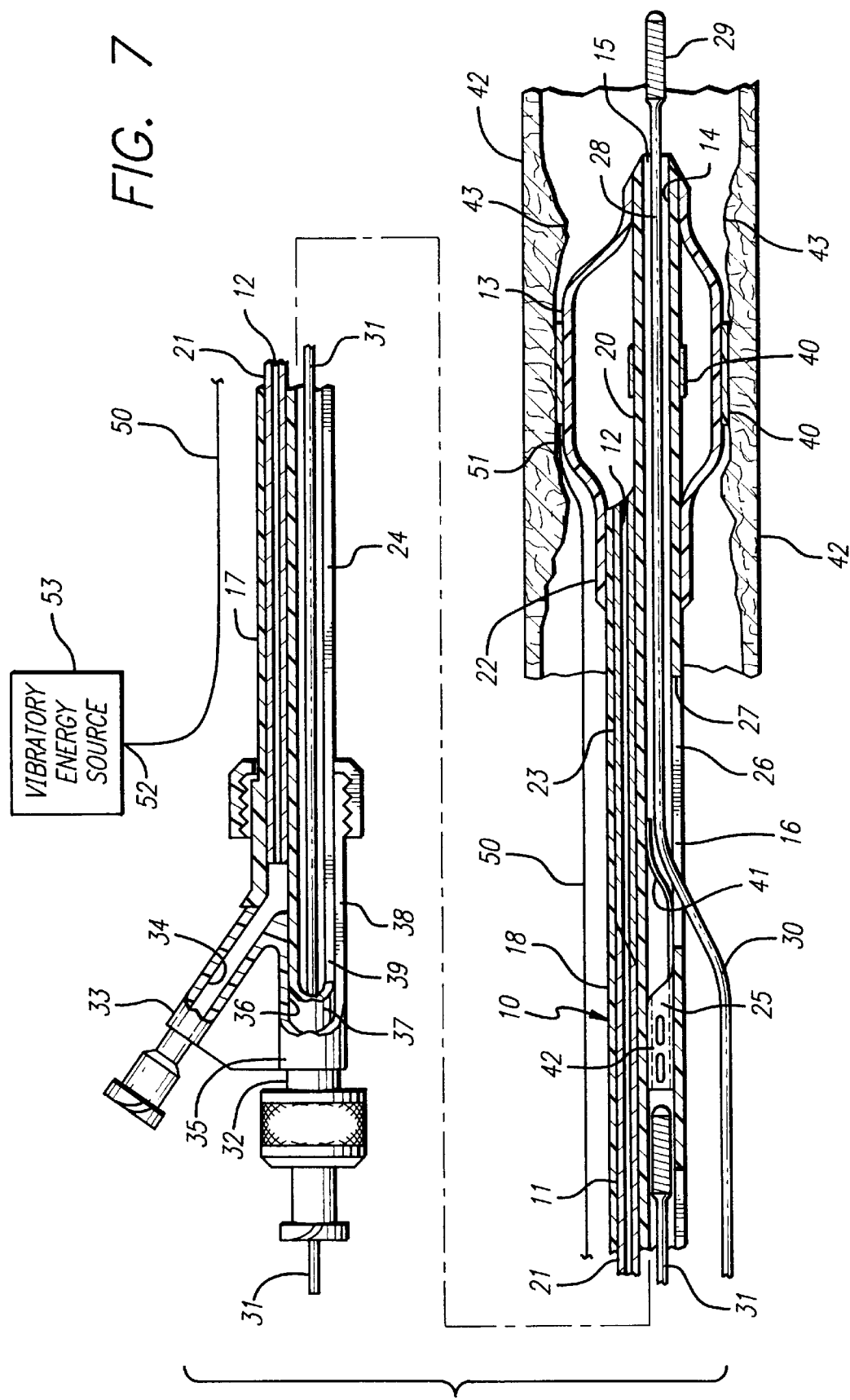

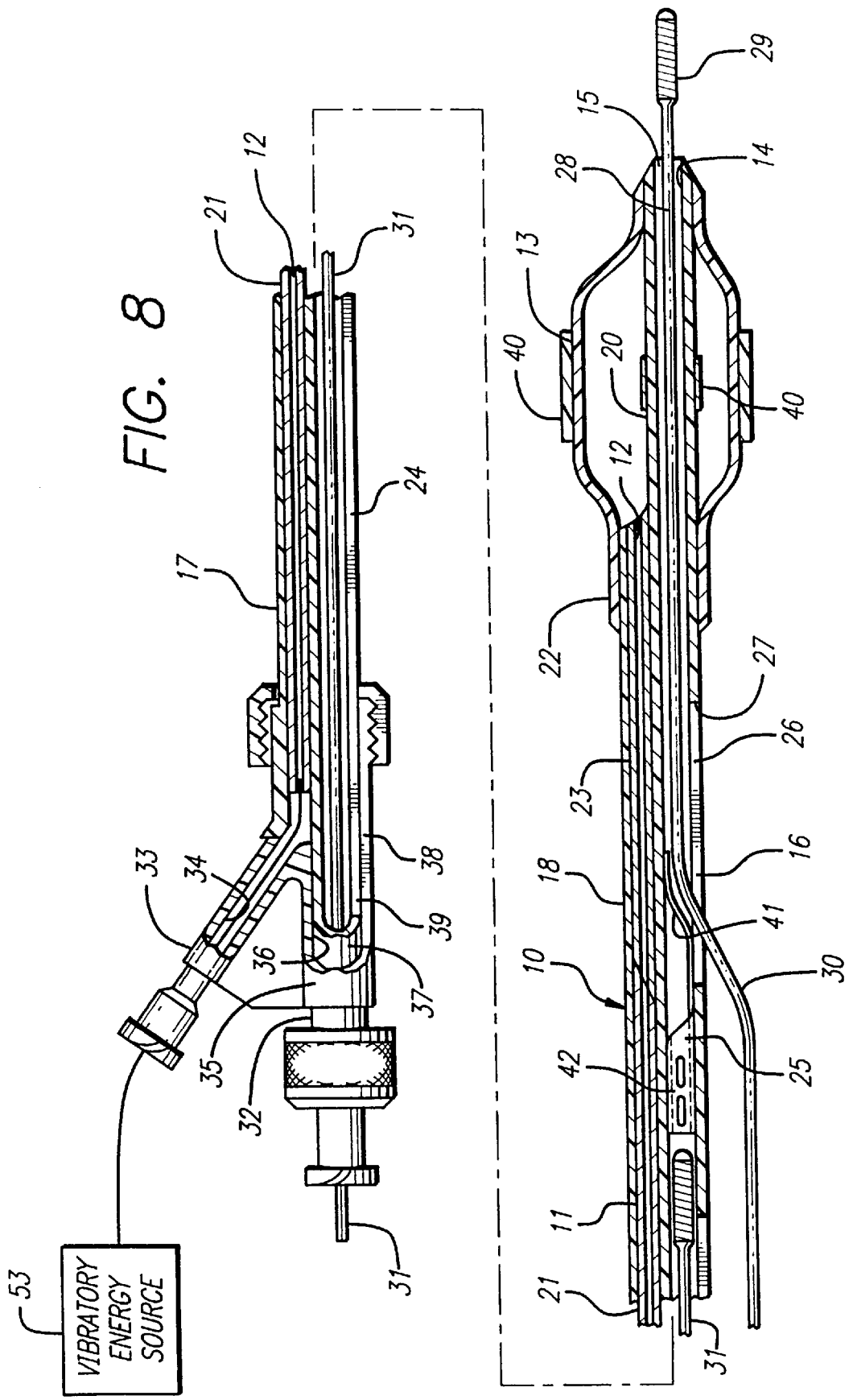

VIBRATING STENT FOR OPENING CALCIFIED LESIONS

BACKGROUND OF THE INVENTION

The invention relates generally to percutaneous transluminal coronary angioplasty (PTCA) in which a dilatation catheter is used to cross a lesion and dilate the lesion area to restore blood flow to the artery. More specifically, the invention relates to a catheter and stent assembly adapted to provide vibratory energy to assist in crossing and dilating calcified lesions.

In typical PTCA procedures, a guiding catheter having a pre-shaped distal tip is percutaneously introduced into the cardiovascular system of a patient and advanced therein until the pre-shaped distal tip thereof is disposed within the aorta adjacent to the ostium of the desired coronary artery. The guiding catheter is twisted or torqued from the proximal end to turn the distal tip of the guiding catheter so that it can be guided into the coronary ostium. A dilatation catheter having a balloon on its distal end and a guide wire slidably disposed within an inner lumen of the dilatation catheter are introduced into and advanced through the guiding catheter to its distal tip. The distal tip of the guide wire is usually manually shaped (i.e., curved) before the guidewire is introduced into the guiding catheter along with the dilatation catheter. The guide wire is first advanced out the distal tip of the guiding catheter, into the patient's coronary artery, and torque is applied to the proximal end of the guide wire, which extends out of the patient, to guide the curved or otherwise-shaped distal end of the guide wire as the guide wire is advanced within the coronary anatomy until the shaped distal end of the guide wire enters the desired artery. The advancement of the guide wire within the selected artery continues until its distal end crosses the lesion to be dilated. The dilatation catheter is then advanced out of the distal tip of the guiding catheter, over the previously advanced guide wire, until the balloon on the distal extremity of the dilatation catheter is properly positioned across the lesion. Once properly positioned, the dilatation balloon is inflated to a predetermined size with radiopaque liquid at relatively high pressures (e.g., 4–12 atmospheres) to dilate the stenosed region of the diseased artery. The balloon is then deflated so that the dilatation catheter can be removed from the dilated stenosis and blood flow can resume through the dilated artery.

Further details of guiding catheters, dilatation catheters, guide wires, and other devices for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson et al.); U.S. Pat. No. 4,554,929 (Samson et al.); U.S. Pat. No. 4,582,185 (Samson); U.S. Pat. No. 4,616,652 (Simpson); U.S. Pat. No. 4,638,805 (Powell); U.S. Pat. No. 4,748,986 (Morrison et al.); U.S. Pat. No. 4,898,577 (Badger et al.); and U.S. Pat. No. 4,827,943 (Taylor et al.), which are hereby incorporated herein in their entirety by reference thereto.

Several notable improvements have recently been made in balloon angioplasty catheters. One such modification, commonly referred to as a rapid-exchange catheter, is described in U.S. Pat. No. 4,748,982 (Horzewski et al.), wherein a short sleeve or inner lumen at least about 10 cm in length is provided within the distal section of the catheter body which extends from a first port proximal to the balloon to a second port in the distal end of the catheter and which is adapted to slidably receive a guide wire. The proximal port is not less than about 10 cm and not more than about 40 cm from the distal end of the catheter. Preferably, a slit is provided in the catheter body extending from the proximal port to a location proximal to the proximal end of the balloon to facilitate the removal of the catheter from the proximal end of the guide wire which extends out of the pattern.

Another modification, which was introduced into the marketplace by the assignee of the present application (Advanced Cardiovascular Systems, Inc.), has been perfusion-type dilatation catheters which allow for long-term dilatations to repair arterial dissections and other arterial damage. These perfusion catheters have a plurality of perfusion ports in the wall forming at least part of the catheter body proximal to the balloon which are in fluid communication with an inner lumen extending to the distal end of the catheter body. A plurality of perfusion ports are preferably provided in the catheter body distal to the balloon which are also in fluid communication with the inner lumen extending to the distal end of the catheter body. When the balloon on the distal extremity of the dilatation catheter is inflated to dilate a stenosis, oxygenated blood in the artery or the aorta or both, depending upon the location of the dilatation catheter within the coronary anatomy, is forced to pass through the proximal perfusion ports, through the inner lumen of the catheter body and out the distal perfusion ports. This provides oxygenated blood downstream from the inflated balloon to thereby prevent or minimize ischemic conditions in tissue distal to the catheter to thereby facilitate long-term dilatations. As a result, care should be exercised in sizing the perfusion ports and the inner lumen to ensure that there is adequate flow of oxygenated blood to tissue distal to the catheter to eliminate or minimize ischemic conditions. Commercially available perfusion catheters generally have relatively large profiles due to the size of the inner tubular member which extends through the interior of the balloon which prevents their use in many distal coronary locations.

A major and continual thrust of development work in the field of intravascular catheters, particularly coronary angioplasty catheters, has been to reduce the profile, i.e., transverse dimensions, of the aforementioned catheters and to improve the flexibility thereof without detrimentally affecting the pushability, particularly in the distal portion of such catheters. A reduction in profile with little or no loss in pushability allows a dilatation catheter to be advanced much further into a patient's coronary vasculature and to cross much tighter lesions.

While the foregoing methods and devices are suitable in most instances to perform a PTCA, especially the prior art low-profile catheters, there exists certain conditions which preclude or at least make PTCA procedures extremely difficult with the prior art devices. For example, when the stenosis (or lesion) in the coronary artery is a near total occlusion, or when the plaque is calcified and essentially blocking almost all blood flow, conventional guide wires and dilatation catheters are unable to cross the stenosis. Complications also can arise if the physician tries to force the guide wire or dilatation catheter through the plaque. Very often, plaque has only one opening through which blood flows, but there are a number of fissures in the plaque. If the physician tries to force the guide wire through a tight lesion, and instead the guide wire follows one of the fissures, then the artery might be perforated as the guide wire follows the fissure instead of the blood flow path. Assuming the guide wire and balloon can cross the stenosis, hard lesions may have calcium in them and typically will require very high balloon pressures to "crack" the lesion and restore blood flow.

Assuming the guide wire is able to cross a tight lesion, there is no guarantee the dilatation catheter will be able to cross, and even if it does cross, it may be difficult or dangerous to the patient to inflate the dilatation balloon at high pressures. The prior art devices offer no solution to this problem of tight lesions, other than to withdraw the guide wire and catheter and then consider alternative procedures such as cardiopulmonary bypass surgery. The present invention is designed to cross nearly occluded arteries and allow the balloon to dilate a calcified lesion more easily and at lower pressures.

SUMMARY OF THE INVENTION

The invention provides a catheter and stent assembly adapted to open calcified lesions using vibratory energy.

The intravascular catheter assembly of the invention includes an elongated tubular member with proximal and distal ends and an expandable member (balloon) near the distal end. An intravascular stent is mounted on the balloon and is crimped down in a first collapsed condition. The balloon and stent are positioned at a stenosed region that is difficult to cross and formed of a calcified or otherwise hardened plaque. A flexible elongated member, such as a wire, extends from outside the patient, through the catheter, and its distal end is positioned near or is in contact with the stent. A vibratory energy source, exterior of the patient, provides vibratory energy along the flexible wire to the stent. The vibratory energy transferred to the stent vibrates the hardened plaque making it easier for the balloon and stent portion of the catheter assembly to dilate the lesion. The vibrating may even partially break up or pulverize the plaque into small particles which will harmlessly be carried away with increased blood flow.

The vibratory energy can be supplied by ultrasound energy that provides continuous energy, pulsed energy, or irregular, non-repetitive energy waves to the flexible wire and hence the stent. The vibratory energy source also can be a mechanical device that produces sufficiently high frequency vibrations to transmit the energy along the flexible wire to the stent, and to the plaque region.

It is desirable to removably attach the flexible wire to the stent so that after the balloon and stent have crossed the lesion, and the stent implanted in the coronary artery, the wire can be detached from the implanted stent and the catheter assembly with the wire withdrawn from the patient.

In one embodiment, the vibratory energy is generated by an audio sound generating device which transmits sound waves through the inflation fluid in the inflation lumen in the catheter. After inflation fluid is injected into the inflation lumen and partially into the balloon, the audio energy source provides vibratory energy to the inflation fluid and hence to the balloon and stent mounted thereon. The vibratory energy again permits the balloon and stent to crack the plaque and more easily dilate the lesion, and may even pulverize a portion of the plaque in the process.

In the preferred method of using the vibratory energy to help dilate the stenosed region, the catheter, with the stent mounted thereon, is first positioned within the stenosed region. A vibratory energy source is supplied to the stent while it is in its collapsed condition on the balloon portion of the catheter, thereby transmitting at least a portion of the vibratory energy through the stent and into the stenosed region. As the stenosed region begins to break up and otherwise provide more of an opening for the distal end of the catheter and the stent, the catheter can be advanced distally so that the balloon and stent are completely positioned within the stenosed region. Continued supplying of vibratory energy will facilitate expansion of the balloon and stent and opening of the body lumen to permit blood flow therethrough. The balloon portion of the catheter is deflated and the catheter and balloon are withdrawn from the body lumen, leaving the stent implanted to assist in holding open the lumen.

These and other advantages of the invention will become more apparent from the following detailed description of the invention when taken in conjunction with the accompanying exemplary drawings.

BRIEF DESCRIPTION OF THE DRAWINGS

FIG. 7 is an elevational view, partially in section, of a rapid-exchange-type catheter embodying features of the invention.

FIG. 8 is an elevational view, partially in section, of a rapid-exchange-type catheter depicting a vibratory energy source for vibrating an expandable stent.

DETAILED DESCRIPTION OF THE PREFERRED EMBODIMENTS

Figure 1:
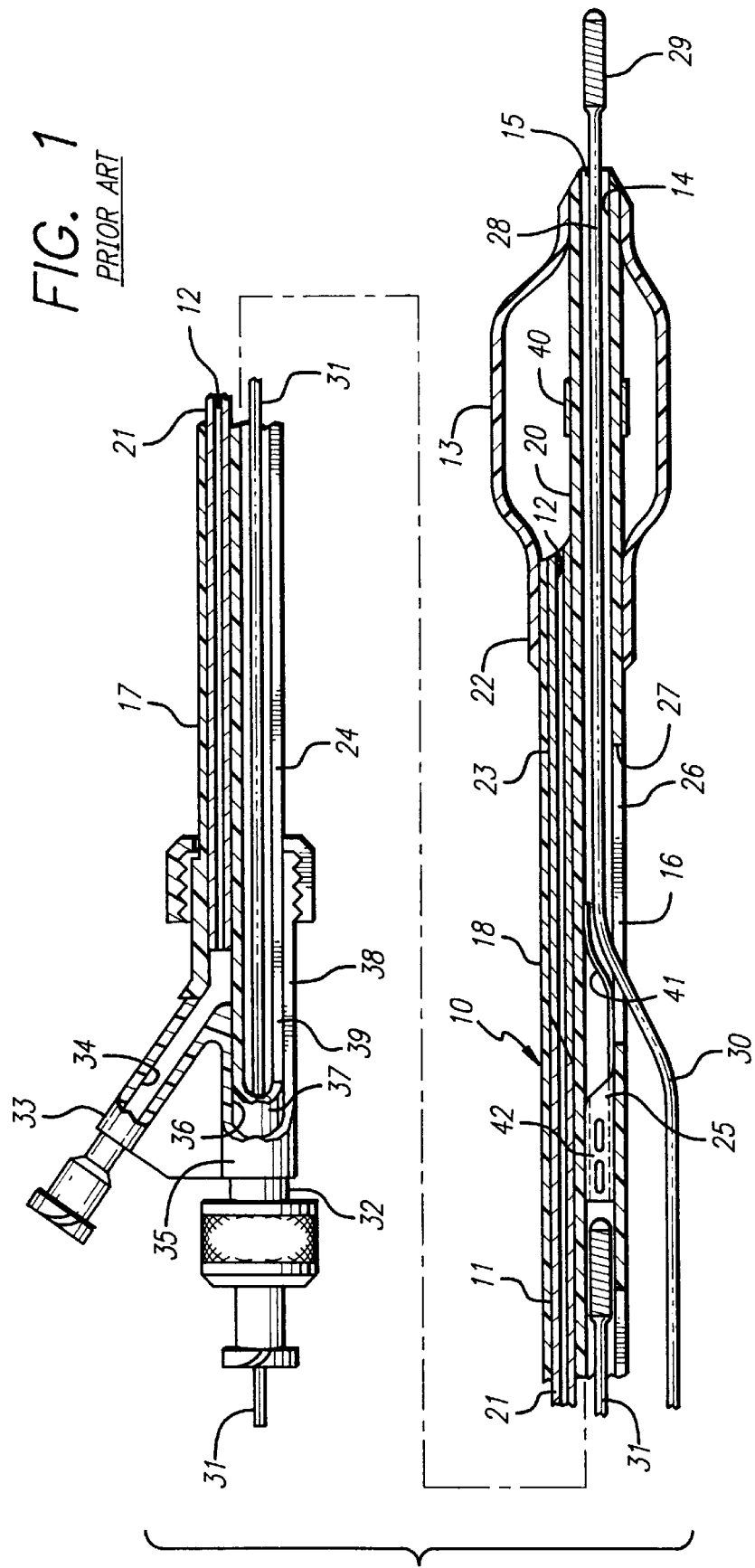
FIG. 1 is an elevational view, partially in section, of a dilation catheter known in the art as a rapid-exchange-type catheter.
Figure 2:
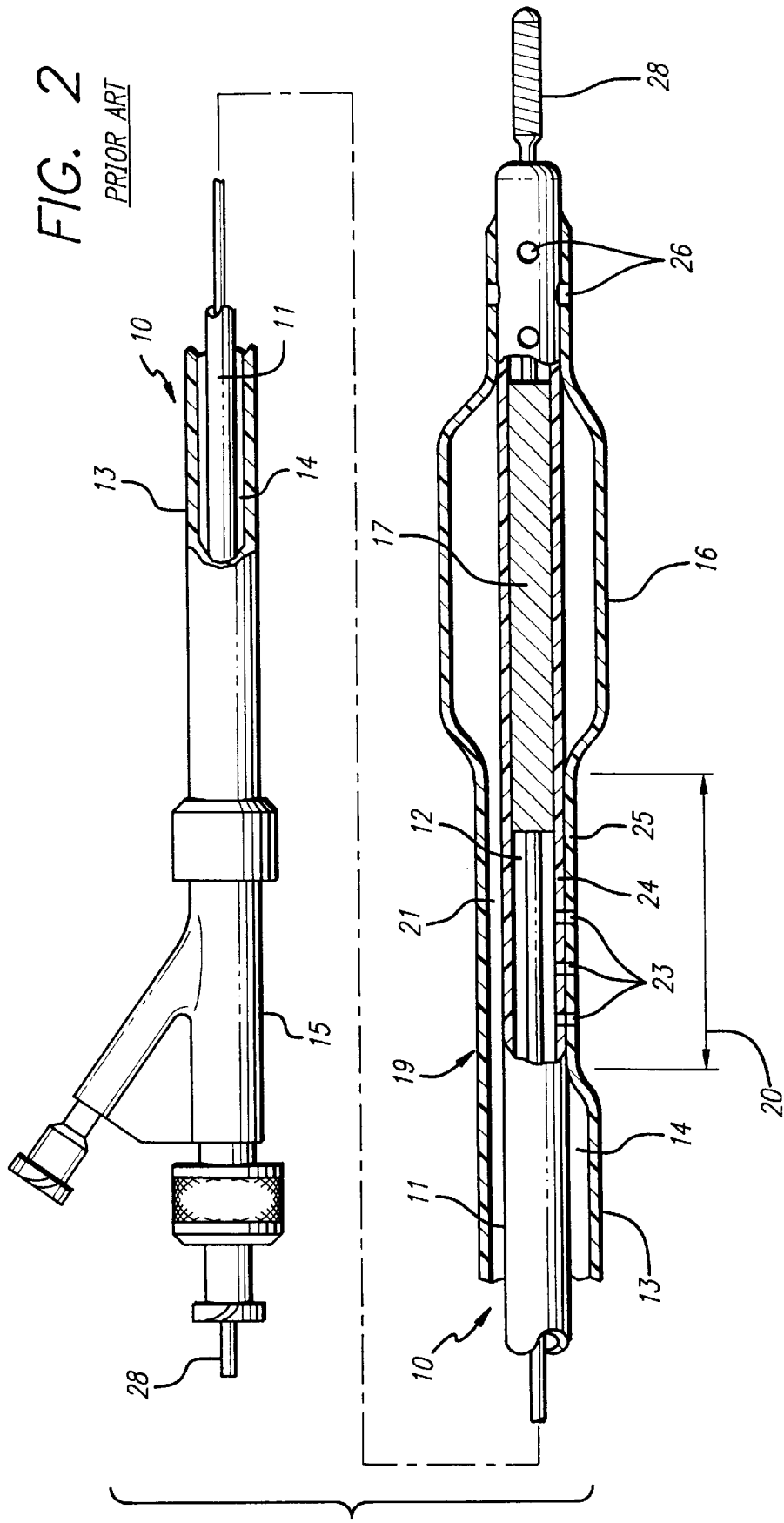
FIG. 2 is an elevational view, partially in section, of a prior art dilatation catheter having perfusion capabilities.

FIG. 1 illustrates a prior art rapid-exchange-type dilatation catheter 10 for use in PTCA procedures which allows for the exchange of a catheter while the guide wire remains in place within a patient's arterial system to avoid loss of the arterial position. This dilatation catheter is typical of the types of catheters used to open tight lesions or partially occluded lesions. Another prior art catheter, as shown in FIG. 2, also can open tight lesions, and has the added feature of being able to perfuse blood while the balloon portion of the catheter is expanded during the PTCA procedure. When the prior art catheters are unable to expand or open a tight or hardened lesion, the present invention can be employed.

Referring to FIGS. 3–7, a preferred embodiment of the catheter and stent system using vibratory energy is depicted. The catheter 10 generally comprises an elongated catheter shaft 11, an inflation lumen 12 adapted to direct inflation fluid from the proximal end of the catheter shaft to the interior of an inflatable balloon 13 on a distal portion of the catheter shaft and a guide wire receiving inner lumen 14 extending therein from the proximal end of the catheter shaft to a first guide wire port 15 in the distal end of the catheter shaft. A second guide wire port 16 which is also in communication with the guide wire lumen 14, is provided in the wall forming at least in part catheter shaft 11 at a location of about 10–50 cm from the distal end of the catheter shaft and a substantial distance from the proximal end of the catheter shaft.

Figures 3, 4, 5, 6:
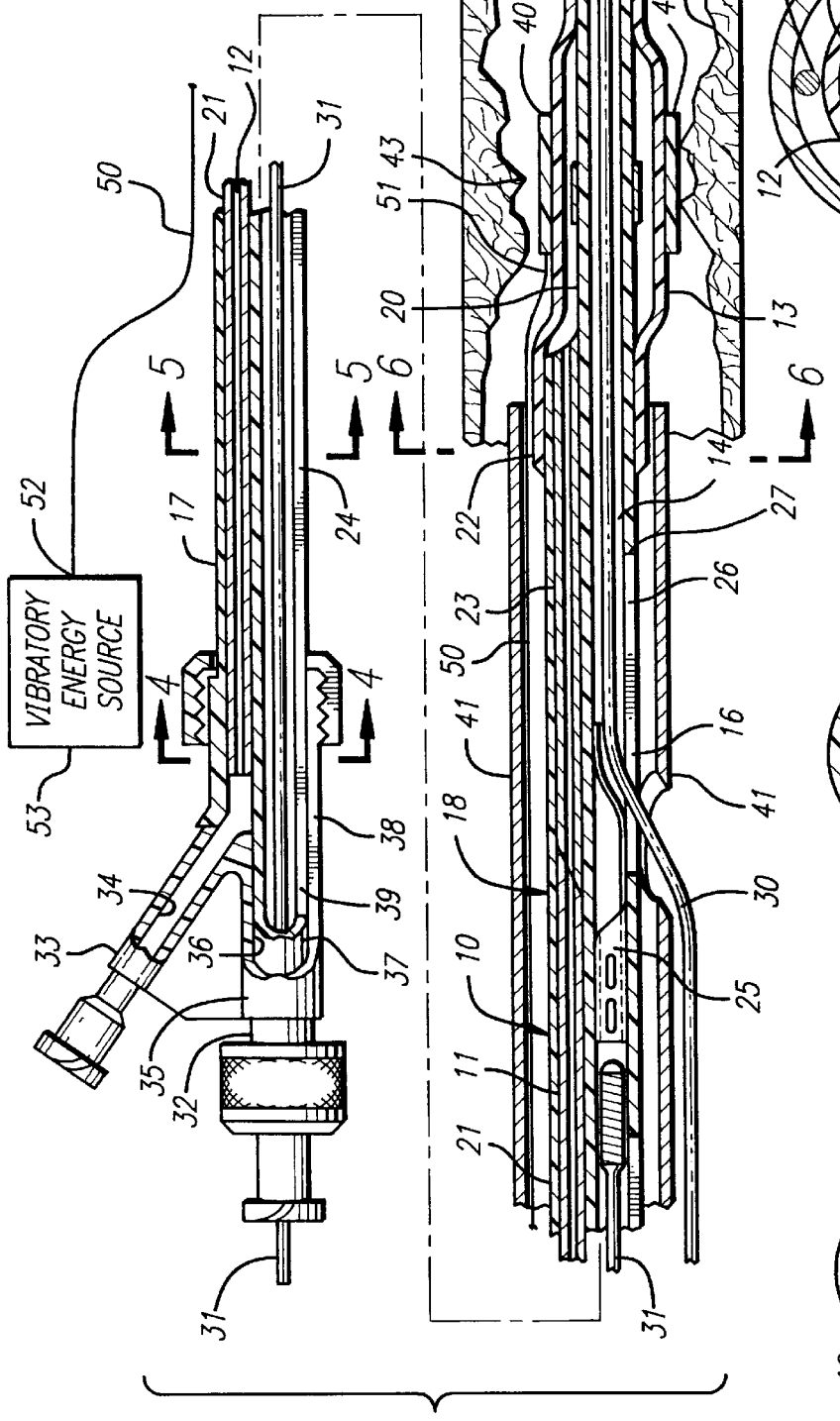
FIG. 3 is a cross-sectional view of a catheter and stent assembly incorporating features of the invention.
FIG. 4 is a transverse, cross-sectional view of the catheter shown in FIG. 3 taken along lines 4—4.
FIG. 5 is a transverse, cross-sectional view of the catheter shown in FIG. 3 taken along lines 5—5.
FIG. 6 is a transverse, cross-section view of the catheter shown in FIG. 3 taken along line 6—6.

As shown in FIGS. 3–7, the proximal section 17 and the distal section 18 of the catheter shaft 11 are of a dual lumen construction with the inflation lumen 12 and guide wire receiving lumen 14 having circular transverse cross-sections. The inflation lumen 12 terminates at the proximal end of the balloon 13 and is in fluid communication with the interior of the balloon. Tubular extension 20 of the catheter shaft 11, which defines in part the guide wire receiving lumen 14, extends to the distal end thereof. The distal end of the balloon 13 is sealingly secured to the distal end of the extension 20 by suitable means such as heat bonding or an adhesive. The inflation lumen 12 within the proximal section 17 is preferably provided with supporting inner tubular member 21 formed of a high strength material such as a polyamide, 20 stainless steel, or a suitable superelastic NiTi alloy. The distal part 23 of the supporting inner tubular member 21 may be formed of a tubular stock with a thinner wall as shown in FIG. 6. The proximal waist 22 of balloon 13 is secured in a suitable manner, such as heat bonding or by an adhesive, to the exterior of the distal section 18 of the shaft 11.

Proximal section 17 of the catheter shaft 11 is provided with a proximal slit 24 which extends from the proximal end of shaft 11 to a location proximal to the guide wire guiding member 25. This construction is typical of a convertible over-the-wire/rapid exchange catheter. The distal catheter shaft section 18 is also provided with distal slit 26 which extends from the second or proximal guide wire port 16 to a location 27 proximal to the proximal waist 22 of balloon 13.

Guide wire 28, which is slidably disposed within inner guide wire lumen 14, has a coil 29 on its distal end which is shown in FIG. 3 extending out of the first guide wire port 15 and an elongated core member 30 which is shown extending through the guide wire member 14 and out of the second guide wire port 16 as would be utilized in a rapid exchange mode. A replacement guide wire 31 is shown within guide wire lumen 14 in the proximal portion of the catheter shaft 11.

A multi-arm adapter 32, which is provided on the proximal end 17 of the catheter shaft 11, has one arm 33 with an inner lumen 34 which is adapted to introduce inflation fluid into the inflation lumen 12 and a second arm 35 with an inner lumen 36 which is adapted to receive a replacement guide wire 31 and guided into the guide wire receiving lumen 14 within the catheter shaft 11. The proximal end of the catheter shaft 11 is provided with an insert 37 which fits into the interior of the adapter 32 as shown. The second arm 35 of adapter 32 is 15 provided with a slit 38 and the insert 37 is provided with a slit 39, both of the slits being continuous with the slit 24 and the proximal section 17 of the catheter shaft 11. A portion of the insert 37 sealingly connects the inner lumen 34 with the inner inflation lumen 12 within the catheter shaft 11. The insert 37 may be formed as a separate element and then secured to the proximal end of the catheter shaft 11 or formed as part of the catheter shaft.

As depicted in FIG. 3, balloon 13 is in its deflated state to provide a low profile for crossing tight lesions. An expandable stent 40 is mounted on balloon 13, generally by compressing the stent by known means so that it is tightly compressed onto the balloon. A protective sheath 41 is provided to cover stent 40 and protect the body lumen 42 from any sharp edges on stent 40, and to help secure stent 40 to balloon 13. Protective sheath 41 is particularly important when advancing a catheter past a tight calcified lesion 43 as depicted in FIG. 3. Protective sheaths 41 are known in the art and are more fully described in commonly owned U.S. Pat. No. 5,458,615 (Klemm et al.). If a protective sheath is used with a rapid exchange catheter, the sheath will have to have a slit for the guide wire to pass through and an opening where the guide wire exits the catheter, at guide wire port 16.

In keeping with the invention, as depicted in FIGS. 3–7, a means for providing vibratory energy to the stent, and hence to the calcified lesion 43, is depicted. A flexible wire 50 is provided for removable connection at its distal end 51 to stent 40. The flexible wire proximal end 52 is connected to vibratory energy source 53 located outside the patient. The vibratory energy source can be an ultrasound device that imparts continuous energy to flexible wire 50, or it can impart pulsed energy to flexible wire 50. Flexible wire 50 can be any metallic wire, such as stainless steel, or nickel titanium, as examples, which are capable of transmitting vibratory energy. The frequency of the vibratory energy is a matter of choice and depends on numerous factors, including the hardness of calcified lesion 43 and other conditions specific to individual patients. It is also envisioned that the vibratory energy source 53 alternatively provide irregular, non-repetitive energy waves to flexible wire 50, which is then transmitted to the stent 40 and calcified lesion 43.

The distal end 51 of wire 50 can be adhesively bonded to balloon 13 and then stent 40 crimped onto the balloon over wire 50. After the vibratory energy is provided and the lesion dilated, the stent remains implanted while the balloon is deflated and along with wire 50 removed from the patient.

In another embodiment of the invention, depicted in FIG. 8, vibratory energy source 53 provides vibratory energy in the form of audio sound waves. The audio sound waves are transmitted from vibratory energy source 53 through the inflation fluid in inflation lumen 12. The inflation fluid will transmit audio sound waves through to the balloon 13 and to stent 40, which will then transmit at least partial vibratory energy to calcified lesion 43.

In keeping with the method of use of the invention, the catheter system of the invention can be inserted into the patient in conventional rapid exchange fashion with guide wire 28 pre-loaded within inner lumen 14 in the distal section 18 and extending proximally out of the proximal guide wire port 16, or it can be inserted in a conventional over-the-wire fashion with the guide wire extending through the entire length of the guide wire lumen 14 and out the second arm 35 of adapter 32. The guide wire 28 and catheter 10 are advanced into the body lumen 42, such as a coronary artery, and advanced to a point up to the calcified lesion 43. As depicted in FIG. 3, the catheter and guide wire are further advanced to be positioned within calcified lesion 43 prior to inflation of balloon 13. Thereafter, balloon 13 is inflated which will expand stent 40 and dilate the calcified lesion 43. As the dilatation procedure commences, vibratory energy from vibratory energy source 53 is transmitted through flexible wire 50, or by audio sound waves (FIG. 8) to assist in partially pulverizing calcified lesion 43, and making inflation of the balloon and stent an easier process. As balloon 13 and stent 40 become fully expanded, as shown in FIG. 7, for example, calcified lesion 43 has been expanded radially outwardly, and because of the vibratory energy transmitted through stent 40, calcified lesion 43 is at least partially pulverized and disintegrated. After body lumen 42 is dilated and stent 40 fully expanded and implanted, balloon 13 is deflated by withdrawing the inflation fluid and the catheter and guide wire are withdrawn from the patient.

The catheter body 11 can be formed by conventional techniques, e.g., extruding, from materials already found useful in intravascular catheters such as polyethylene, polyvinyl chloride, polyesters and composite materials. The various components of the catheter can be joined by suitable adhesive such as the acrylonitrile-based adhesive sold as Loctite™ 405. Heat shrinking or heat bonding may also be employed where appropriate.

The size of the catheter body 11 and the guide-wire-receiving inner lumen 14 thereof to a large extent are determined by the size of the guide wires 28 and 31 to be employed and the size of the artery or other body lumen through which the catheter must pass. The catheter body 11 is sufficiently long to extend from outside the proximal end of a guiding catheter, which likewise extends out of the patient, to a stenosis to be treated within the patient's vascular system (or other desired location therein), from about 100 to 150 cm when a Sledinger approach through the femoral artery is employed to introduce a catheter 10 into the patient's vasculature. The wall forming the catheter must be of sufficient thickness and strength so that it can be pushed over the guide wire 28 (or 31) to the desired location within the patient's blood vessel.

It is to be understood that while PTCA procedures have been discussed herein in connection with the invention, any body lumen can be treated according to the method and apparatus claimed. Thus, the invention can be used to treat calcified or tight lesions in arteries, veins, blood vessels, coronary arteries, carotid arteries, peripheral veins, bile ducts, the aorta, and virtually any body lumen.

While the invention has been described herein in terms of certain presently-preferred embodiments directed to catheters for opening calcified lesions and for implanting a stent therein, those skilled in the art will recognize that the catheter of the invention may be used in a variety of body lumens. Further, although a rapid-exchange and perfusion-type catheter was described herein, other types of catheters, such as over-the-wire catheters can be employed for use with the invention for vibrating calcified lesions. Other modifications and improvements may be made to the invention without departing from the scope thereof.

What is claimed is:

1. An apparatus for imparting vibratory energy to a stenosed region in a body lumen, comprising:
    a generally tubular and radially expandable stent having a first collapsed condition and a second expanded condition, and adapted to be positioned in contact with the stenosed region of the body lumen:
    a source of vibratory energy; and
    a flexible elongated member having a proximal end and a distal end and coupled at the proximal end exterior of the body to the energy source and at the distal end to the stent, whereby vibratory energy from the source is transmitted through the flexible elongated member and the stent to the stenosed region.

2. The apparatus of claim 1, wherein the vibratory energy is generated by an ultrasound device.

3. The apparatus of claim 2, wherein the ultrasound device imparts continuous energy to the flexible elongated member and the stent and therefore to the stenosed region.

4. The apparatus of claim 2, wherein the ultrasound device imparts pulsed energy to the flexible elongated member and the stent and therefore to the stenosed region.

5. The apparatus of claim 2, wherein the ultrasound device imparts irregular, non-repetitive energy waves to the flexible elongated member and the stent and therefore to the stenosed region.

6. The apparatus of claim 1, wherein the vibratory energy is generated by an audio sound generating device, and wherein the flexible elongated member is an inflation lumen.

7. The apparatus of claim 1, wherein the stent is configured to be permanently implanted in the body lumen.

8. The apparatus of claim 1, wherein the stent is configured to be removably implanted in the body lumen.

9. The apparatus of claim 1, wherein the stent is configured to be temporarily positioned in the body lumen.

10. The apparatus of claim 1, wherein the flexible elongated member distal end is attached to the stent.

11. The apparatus of claim 1, wherein the flexible elongated member distal end is adjacent the stent, but not in physical contact.

12. The apparatus of claim 1, wherein the flexible elongated member distal end is in physical contact with the stent.

13. An apparatus for imparting vibratory energy to a stenosed region in a body lumen, comprising:
    a generally tubular and radially expandable stent having a first collapsed condition and a second expanded condition, and adapted to be positioned in contact with the stenosed region of the body lumen;
    a vibratory energy source for providing vibratory energy;
    a catheter having a distal end, a proximal end, an expandable region at the catheter distal end, and a fluid lumen extending through the catheter and in fluid communication with the expandable region, the stent being mounted on the expandable region in the first collapsed condition; and
    a flexible elongated member having a proximal end and a distal end, the flexible elongated member coupled at the proximal end exterior of the body to the vibratory energy source, and the flexible elongated member distal end terminates within the expandable region, whereby inflation liquid is introduced through the fluid lumen to expand the expandable region and thereby expand the stent from the first collapsed condition to the second expanded condition and whereby vibratory energy from the vibratory energy source transfers at least some of the vibratory energy through the inflation fluid in the expandable region to the stent and therefore to the stenosed region.

14. The apparatus of claim 13, wherein the vibratory energy is generated by an ultrasound device.

15. The apparatus of claim 14, wherein the ultrasound device imparts continuous energy to the flexible elongated member and therefore to the stenosed region.

16. The apparatus of claim 14, wherein the ultrasound device imparts pulsed energy to the flexible elongated member and therefore to the stenosed region.

17. The apparatus of claim 14, wherein the ultrasound device imparts irregular, non-repetitive energy waves to the flexible elongated member and therefore to the stenosed region.

18. A method for imparting vibratory energy to plaque forming a stenosed region in a body lumen, the method comprising:
    providing a generally tubular and radially expandable stent having a first collapsed condition and a second expanded condition;
    positioning the stent in the collapsed condition in contact with the stenosed region;
    supplying vibratory energy to the stent while in the collapsed condition, thereby transmitting at least a portion of the vibratory energy through the stent and into the stenosed region; and
    expanding the stent to the second expanded condition to dilate the body lumen in the area of the stenosed region.

19. The method of claim 18, wherein the vibratory energy is generated by an ultrasound device.

20. The method of claim 18, wherein the vibratory energy is generated by a mechanical device, and wherein the vibratory energy is transmitted to the stent through a control wire removably attached to the stent and thereby transmitted to the stenosed region of the body lumen.

21. A method for imparting vibratory energy to plaque forming a stenosed region in a body lumen, the method comprising:

providing a catheter having a distal end, a proximal end, an expandable region at the catheter distal end, and a fluid lumen extending through the catheter and in fluid communication with the expandable region; providing a generally tubular and radially expandable stent having a first collapsed condition and a second expanded condition; the stent being mounted on the expandable region in the first collapsed condition;

positioning the stent and the expandable region in their respective collapsed condition in the stenosed region;

inserting an inflation liquid into the expandable region to partially expand the expandable region and the stent into contact with the stenosed region;

supplying ultrasound energy to the inflation liquid in the expandable region thereby transmitting vibratory energy to the stent in its partially expanded condition, and thereby further transmitting at least a portion of the vibratory energy to the stenosed region;

expanding the stent further to the second expanded condition to dilate the stenosed region of said body lumen;

deflating the expandable region; and withdrawing the catheter and the expandable region from the body lumen.

22. An apparatus for imparting vibratory energy to a stenosed region in a body lumen, comprising:

a generally tubular and radially expandable stent having a first collapsed condition and a second expanded condition, and adapted to be positioned in contact with the stenosed region of the body lumen:

a source of vibratory energy including a mechanical vibratory device; and a flexible elongated member having a proximal end and a distal end and coupled at the proximal end exterior of the body to the energy source and at the distal end to the stent, the flexible elongated member including a control wire removably coupled to the stent, whereby vibratory energy from the source is transmitted through the flexible elongated member and the stent to the stenosed region.

* * * * *

UNITED STATES PATENT AND TRADEMARK OFFICE
CERTIFICATE OF CORRECTION

PATENT NO.    : 6,083,232
DATED         : July 4, 2000
INVENTOR(S)   : Daniel L. Cox It is certified that error appears in the above-identified patent and that said Letters Patent is hereby corrected as shown below:

<u>Title page,</u>
Item [73], "Assignee", change "Cardivascular", to read -- Cardiovascular --.

Signed and Sealed this

Twenty-seventh Day of August, 2002

Attest:

Attesting Officer

JAMES E. ROGAN
Director of the United States Patent and Trademark Office